US011165092B2

(12) United States Patent
Konno et al.

(10) Patent No.: US 11,165,092 B2
(45) Date of Patent: Nov. 2, 2021

(54) IONIC SOLID

(71) Applicant: JAPAN SCIENCE AND TECHNOLOGY AGENCY, Kawaguchi (JP)

(72) Inventors: Takumi Konno, Toyonaka (JP); Nobuto Yoshinari, Toyonaka (JP)

(73) Assignee: JAPAN SCIENCE AND TECHNOLOGY AGENCY, Kawaguchi (JP)

(*) Notice: Subject to any disclaimer, the term of this patent is extended or adjusted under 35 U.S.C. 154(b) by 217 days.

(21) Appl. No.: 16/345,052

(22) PCT Filed: Oct. 31, 2017

(86) PCT No.: PCT/JP2017/039329
§ 371 (c)(1),
(2) Date: Aug. 6, 2019

(87) PCT Pub. No.: WO2018/079831
PCT Pub. Date: May 3, 2018

(65) Prior Publication Data
US 2019/0359642 A1    Nov. 28, 2019

(30) Foreign Application Priority Data
Oct. 31, 2016  (JP) .............. JP2016-212460

(51) Int. Cl.
*H01M 10/052* (2010.01)
*H01M 10/0562* (2010.01)
(Continued)

(52) U.S. Cl.
CPC ......... *H01M 10/052* (2013.01); *C07F 19/005* (2013.01); *G02F 1/1516* (2019.01); *H01M 10/0562* (2013.01); *H01M 2300/0071* (2013.01)

(58) Field of Classification Search
CPC ............ H01M 10/052; H01M 10/0562; G02F 1/1516; C07F 19/005
See application file for complete search history.

(56) References Cited

U.S. PATENT DOCUMENTS

2007/0160911 A1    7/2007    Senga et al.
2010/0133487 A1    6/2010    Kawamoto et al.

FOREIGN PATENT DOCUMENTS

CN    105860088 A    8/2016
EP    2 116 511 A1    11/2009
(Continued)

OTHER PUBLICATIONS

International Search Report dated Dec. 12, 2017, in PCT/JP2017/039339, citing documents AU, AV and AW therein, 7 pages (with Translation of Category of Cited Documents).
(Continued)

Primary Examiner — James Lee
(74) Attorney, Agent, or Firm — Oblon, McClelland, Maier & Neustadt, L.L.P.

(57) ABSTRACT

Provided are a novel ionic solid usable for a secondary battery and demonstrating a high ionic conductivity, and an ionic conductor containing the same. An ionic solid, wherein an anionic heterometallic complex composed of one metal $M^1$ selected from the group consisting of Ir, Rh, Co, Os, Ru, Fe, Ni, Cr and Mn, one metal $M^2$ selected from the group consisting of Zn, Cd, Hg, Au, Ag and Cu (provided that when $M^1$ is Rh, $M^2$ is not Zn) and a ligand aggregates to form a crystal lattice in which a cationic species is present in an interstice in the crystal lattice.

12 Claims, 5 Drawing Sheets

(51) Int. Cl.
    *G02F 1/1516*    (2019.01)
    *C07F 19/00*    (2006.01)

(56) References Cited

FOREIGN PATENT DOCUMENTS

| JP | 2005-228570 A | 8/2005 |
|---|---|---|
| JP | 2008-4459 A | 1/2008 |
| JP | 2015-176854 A | 10/2015 |
| JP | 2016-50133 A | 4/2016 |
| JP | 2016-110792 A | 6/2016 |
| WO | WO 2008/081923 A1 | 7/2008 |

OTHER PUBLICATIONS

Yoshinari, N. et al., "Cation-exchange Reaction on Single Crystals of an Anionic RhIII4ZnII4 Octanuclear Complex with L-Cysteinate". The Abstract of the 66th Forum of Japan Society of Coordination Chemistry, 2PA-032. Aug. 20. 2016, 5 pages (with English translation).

Yoshinari, N. et al., "Proton Conductivity of Ionic Solids Composed of L-Cysteinalo RhIIIH4ZnII4 Octanuclear Clusters", The Abstract of the 62nd Forum of Japan Society of Coordination Chemistry, 2PA-097, Sep. 1, 2012, 4 pages (with English translation).

Konno, T. et al., "Synthesis and Properties of T-Cage-Type S-Bridged RhIII4ZnII4 Octanuclear Complexes wih 2-Aminoethsnethiotate or L-Cysteinate", Inorg. Chem , vol. 33. No 3, 1994. pp. 538-544.

Yoshinari, N. et al., "Ionic Conductivities of Alkaline Metal Salts of a RhIII4ZnII4 Octanuclear Complex with L-Cysteinate", The Abstract of the 65Japan Society of Coordination Chemistry Symposium, 3Aa-03, Sep. 2015. 1 page.

Yoshinari, N. et al., "A1:1 Intercluster compound consisting of +6 and −6 charged RhIII4ZnII4 octanuclear cattons and anions with aminothiolate ligands", CrystEngComm, vol. 15. 2013, p. 10016-10019.

Office Action dated Jul. 23, 2020 for Chinese Patent Application No. 201780067425.6 (with machine translation obtained through Espacenet).

Pei-Shan Lee, et al., "Difference in Chiral Recognition Behavior between $Ag^I_3M^{III}_2$ and $Au^I_3,M^{III}_2$ 2 (M = Co, Rh) Anionic Complexes with L-Cysteinato" Chemistry Letters, vol. 45, Apr. 22, 2016, pp. 740-742 with supporting information.

Ukyo Yamashita, et al., "Conversion of $_{L-Cysteinato Rh}{}^{III}_4Zn^{II}_4$ Octanuclear to $Rh^{III}_2$ $Ag^I_3$ Pentanuclear Structure by $Ag^I$ Ions" Bulletin of the Chemical Society of Japan, vol. 86, No. 12, Dec. 15, 2013, pp. 1450-1452 with supporting information.

Takumi Konno, et al., "Preparation and Properties of S-Bridged $Co^{III}Ag^I_3Co^{III}$ Pentanuclear Complexes Having a Triple Helical Chirality. Crystal Structure of $[Ag_3\{Co(aet)_3\}_2](BF_4)_3$ (aet = 2-Aminoethanethiolate)" Bulletin of the Chemical Society, vol. 71, No. 5, 1998, pp. 1049-1054.

Pei-Shan Lee, et al., "pH-Controlled Multiple Chiral Inversion That Induces Molecular Dimerization in a Gold(I)—Cobalt(III) Coordination System with $_L$-Cysteinato" Chemistry—A European Journal, vol. 20, Issue 22, pp. 1-4 with supporting information.

Takumi Konno, et al., "Preparation and Some Properties of $[Co^{III}$ $^{or III}\{Rh^{III}$ (aet orL-cys-N,S)$_3\}_2]$-Type S-Bridged Trinuclear Complexes" Bulletin of the Chemical Society of Japan, vol. 63, No. 3, 1990, pp. 792-798.

[Figure 1]
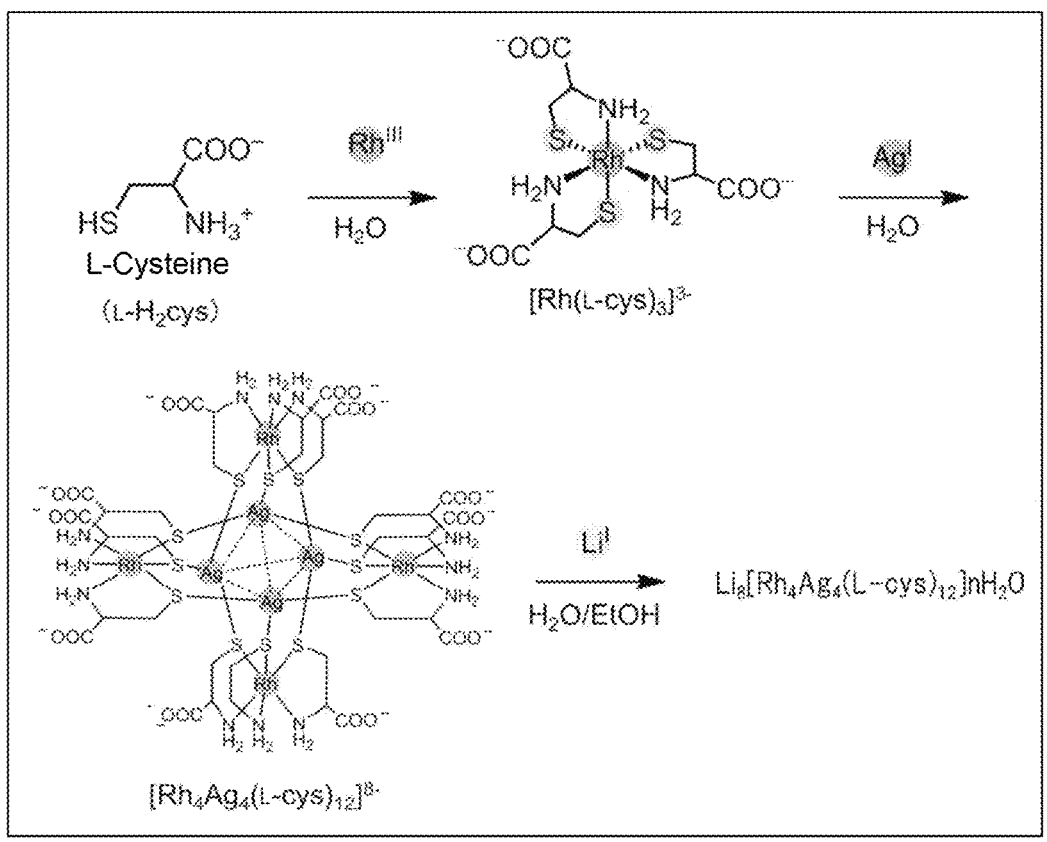

[Figure 2]
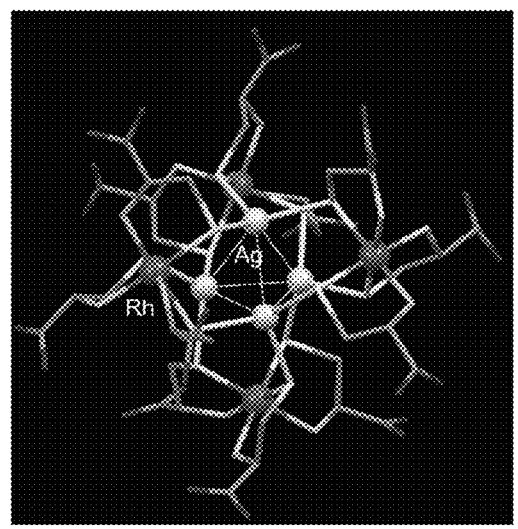
Molecular structure of [Rh₄Ag₄(L-cys)₁₂]⁸⁻
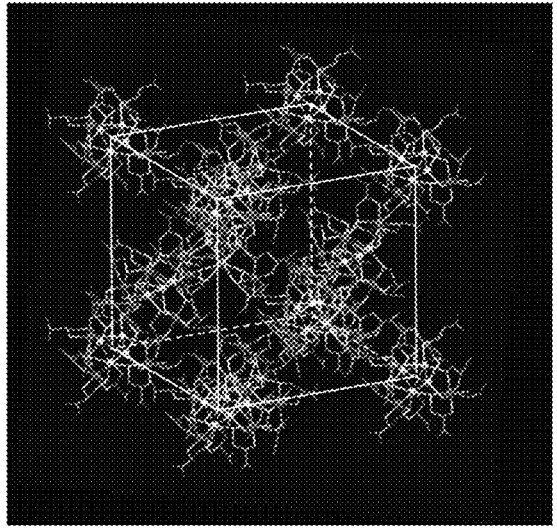
Packing structure of Li₈[Rh₄Ag₄(L-cys)₁₂]

[Figure 3]
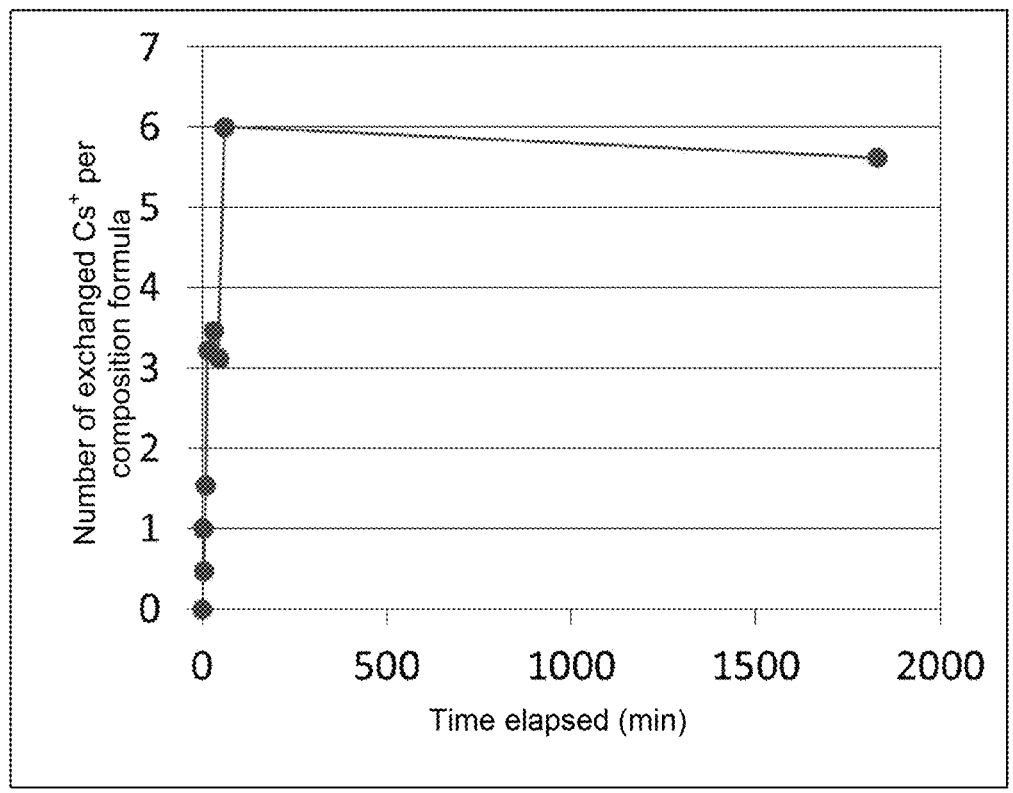

[Figure 4]
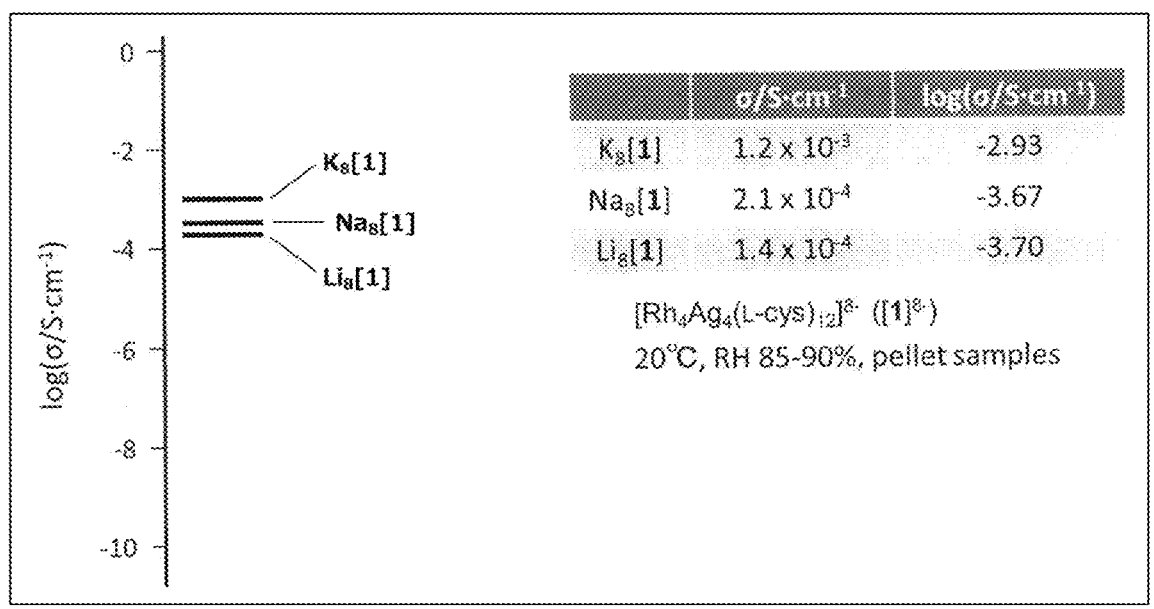

[Figure 5]
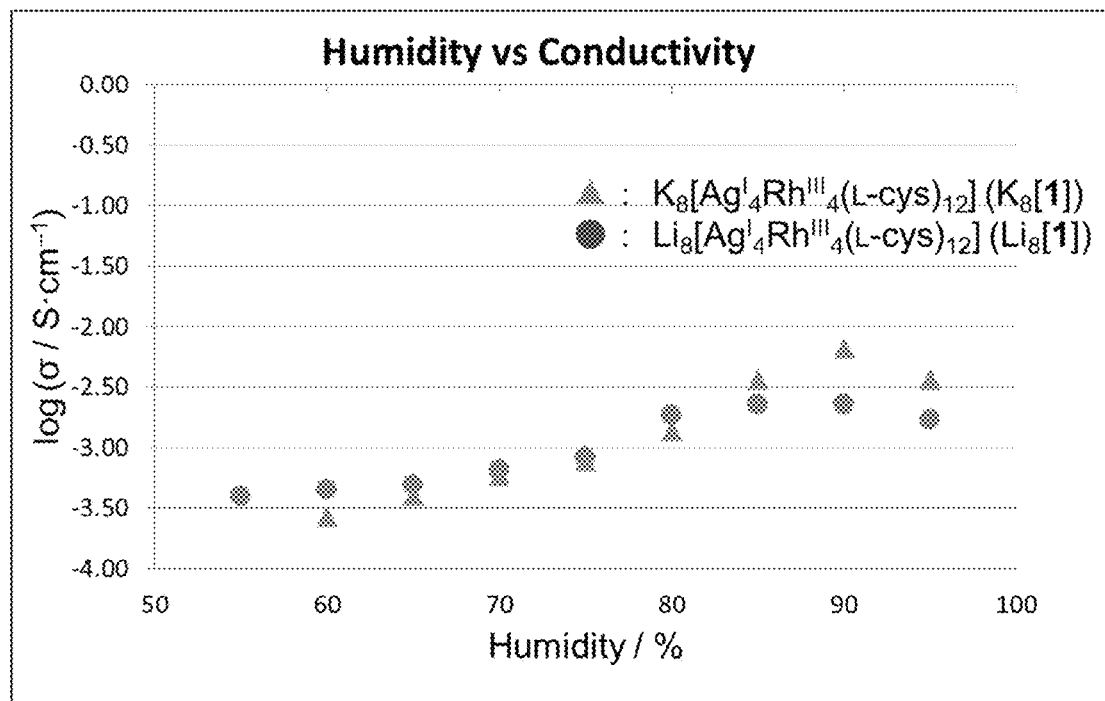

IONIC SOLID

FIELD OF THE INVENTION

The present invention relates to an ionic solid and an ionic conductor using the same, and a cation separating agent.

BACKGROUND OF THE INVENTION

Lead-acid batteries have constituted the mainstream as chargeable/dischargeable secondary batteries, but mobile phones and laptop computers have been developed and accordingly high-capacity, small and lightweight lithium-ion secondary batteries are used. Lithium-ion secondary batteries widely used at present use a lithium-transition metal composite at a positive electrode, a carbon material at a negative electrode, and a lithium salt dissolved in an organic solvent as an electrolyte. When this lithium-ion secondary battery is charged fast or excessively, heat is generated at the positive electrode side due to the oxidation of electrolytic solution and the destruction of crystal structure while metallic lithium precipitates at the negative electrode side. As a result, both electrodes are directly connected to cause a short circuit, and cause explosion and ignition in the worst case.

Under the circumstance, all-solid secondary batteries using a solid electrolyte as an electrolyte have been developed in recent years. Known solid electrolytes having been reported so far include lithium sulfide-based electrolytes (Patent Literatures 1 and 2) and lithium oxide-based electrolytes (Patent Literatures 3 and 4).

Studies on new functions of metal complexes have also been conducted recently, and for example, a Prussian blue type complex $(AxM^A M^B[(CN)_6]y.zH_2O)$ has been studied as a color development inhibitor, an ionic conductor and the like (Patent Literatures 5 and 6). Further, the present inventors synthesized some metal complexes which demonstrate ionic conduction properties and published them (Non Patent Literatures 1 to 3).

Patent Literature 1: JP-A-2005-228570
Patent Literature 2: JP-A-2008-4459
Patent Literature 3: JP-A-2015-176854
Patent Literature 4: JP-A-2016-110792
Patent Literature 5: International Publication No. WO2008/081923
Patent Literature 6: JP-A-2016-50133
Non Patent Literature 1: the 65th Japan Society of Coordination Chemistry Symposium (September, 2015, Nara Women's University) 3Aa-03 ionic Conductivities of Alkaline Metal Salts of a RhIII4ZnII4 Octanuclear Complex with L-cysteinate
Non Patent Literature 2: Inorg. Chem., 1994, 33, 538.
Non Patent Literature 3: Cryst. Eng. Comm., 2013, 15, 10016-10019

SUMMARY OF THE INVENTION

Technical Problem

However, the above lithium sulfide-based electrolytes have not been used practically because hydrogen sulfide is generated. On the other hand, the lithium oxide-based electrolytes, which are also based on ceramic, must be treated at a high temperature close to 1,000° C. for molding, and therefore unsuitable for the production of battery devices. Additionally, a Prussian blue type metal complex demonstrates proton conduction properties as described in Patent Literature 6 but it does not demonstrate metal ionic conduction properties, and thus cannot be used for secondary batteries. Further, the metal complexes described in Non Patent Literatures 1 to 3 failed to demonstrate sufficient ionic conductivity when produced as a molded product to be used for batteries and the like.

Accordingly, an object of the present invention is to provide a novel ionic solid usable for a secondary battery and demonstrating a high ionic conductivity, and an ionic conductor comprising the same.

Solution to Problem

The present inventors have produced various metal complexes and studied on properties and functions thereof and found that an ionic solid represented by the following Formula (1), wherein an anionic heterometallic complex aggregates to form a crystal lattice in which a cationic species is present in an interstice in the crystal lattice, is stable against moisture and humidity with the cationic species being highly mobile, demonstrates an extremely high metal ionic conductivity even when produced as a practical molded product such as pellets, and has the function of fast exchanging cations such as a cesium ion, and is thus useful as an ionic conductor, a solid electrolyte, and a cation separating agent, leading to completion of the present invention.

More specifically, the present invention is to provide the following [1] to [13].

[1] An ionic solid, wherein an anionic heterometallic complex comprising one metal $M^1$ selected from the group consisting of Ir, Rh, Co, Os, Ru, Fe, Ni, Cr and Mn, one metal $M^2$ selected from the group consisting of Zn, Cd, Hg, Au, Ag and Cu (provided that when $M^2$ is Rh, $M^2$ is not Zn) and a ligand aggregates to form a crystal lattice in which a cationic species is present in an interstice in the crystal lattice.

[2] An ionic solid represented by Formula (1):

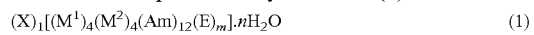

$$(X)_l[(M^1)_4(M^2)_4(Am)_{12}(E)_m].nH_2O \qquad (1)$$

wherein $M^1$ is Zr, Rh, Co, Os, Ru, Fe, Ni, Cr or Mn;
$M^2$ is Zn, d, Hg, Au, Ag or Cu (provided that when $M^2$ is Rh, $M^2$ is not Zn);
X is a cation;
Am is an amino acid;
E is $O^{2-}$, $S^{2-}$, $Se^{2-}$, $Te^{2-}$, $F^-$, $Cl^-$, $Br^-$ or $I^-$;
l is a number ranging from 4 to 14 when multiplied by an ionic valence of X;
m is a number of 0 or 1; and
n is a number of 1 to 100.

[3] The ionic solid according to [1] or [2], wherein the anionic heterometallic complex is a complex represented by Formula (2):

$$[(M^1)_4(M^2)_4(Am)_{12}(E)_m]^{1-} \qquad (2)$$

wherein $M^1$ is Ir, Rh, Co, Os, Ru, Fe, Ni, Cr or Mn;
$M^2$ is Zn, Cd, Hg, Au, Ag or Cu (provided that when $M^2$ is Rh, $M^2$ is not Zn);
X is a cation;
Am is an amino acid;
E is $O^{2-}$, $S^{2-}$, $Se^{2-}$, $Te^{2-}$, $F^-$, $Cl^-$, $Br^-$ or $I^-$;
l is a number ranging from 4 to 14 when multiplied by an ionic valence of X; and
m a number of 0 or 1.

[4] The ionic solid according to [2] or [3], wherein Am is an amino acid having a thiol group.

[5] The ionic solid according to any of [2] to [4], wherein X is a cation of a metal belonging to Group 1 or Group 2.

[6] The ionic solid according to any of [2] to [5], wherein M¹ is Rh or Co, and M² is Ag or Zn.

[7] The ionic solid according to any of to [6], wherein Am is an amino acid selected from the group consisting of cysteine, penicillamine and homocysteine.

[8] An ionic conductor comprising the ionic solid according to any of [1] to [7].

[9] A solid electrolyte comprising the ionic solid according to any of [1] to [7].

[10] An electrochemical device comprising the ionic conductor according to [8].

[11] The electrochemical device according to [10], which is an electrochemical device selected from the group consisting of an ion secondary battery, an electrochromic element and a thermoelectric element.

[12] A cation separating agent comprising the ionic solid according to any of [1] to [7].

[13] The cation separating agent according to [12], which is a radioactive cesium ion separating agent.

Advantageous Effects of the Invention

An ionic solid of the present invention is stable against moisture, easily pelletized and demonstrates excellent ionic conduction properties in the state of a molded product such as pellets, thereby to be useful as a material for an electrochemical device such as an ion secondary battery, an electrochromic element and a thermoelectric element.

Additionally, the ionic solid of the present invention fast exchanges cations such as radioactive cesium ions and thus is useful as a separating agent of cations represented by radioactive cesium ions.

BRIEF DESCRIPTION OF DRAWINGS

FIG. 1 is a drawing showing the reaction of Example 1.

FIG. 2 is drawings showing a crystal structure of the ionic solid obtained in Example 1.

FIG. 3 is a drawing showing an exchange capacity of the ionic solid obtained in Example 2 onto cesium ion.

FIG. 4 is a drawing showing ion conductivities of pellet samples of the ionic solids obtained in Examples and 2.

FIG. 5 is a drawing showing humidity dependency of the ionic conductivity of an ionic solid of the present invention.

DETAILED DESCRIPTION OF THE INVENTION

An ionic solid of the present invention is one in which an anionic heterometallic complex forms a crystal lattice and a cationic species is present in an interstice in the crystal lattice. The cationic species being present in an interstice in the crystal lattice refers to a condition in which a cationic species is present at a free position in an interstice in the crystal lattice, whereas the anionic heterometallic complex is held at a specific position forming the crystal lattice. When an electric field is applied to an ionic solid of the present invention, a cationic species can migrate through the ionic solid, thereby demonstrating the so-called ionic fluidity. The ionic solid of the present invention is a solid electrolyte and also serves as an ion exchanger, same as general ionic solids.

In general ionic crystals, a cationic species and an anionic species have ion sizes close to each other and thus Coulomb attraction works effectively to completely fix the positions of the cationic species and the anionic species. For this reason, neither the cationic species nor the anionic species can move, thus resulting in no fluidity. On the other hand, the ionic solid of the present invention can ensure high mobility of the cationic species by the means described below.

First, an anionic species having a large ion size is used to decrease the surface charge density of the anionic species and reduce the cation-anion Coulomb attraction.

Second, water molecules are incorporated in the structure; with this, the water molecules are allowed to go between cations and anions to reduce the Coulomb attraction by the high dielectric constant of water.

Third, a substituent beneficial for non-Coulomb interaction (for example, an amino group and a carboxyl group capable of forming a hydrogen bond) is coordinated to anionic heterometallic complexes to connect the anionic complexes with each other for forming a limitlessly expanding "pathway" required for the mobility of a cationic species. Particularly when a complex anion having a spherical structure is used, a pathway unbreakable even under an external pressure is spontaneously formed between adjacent complex anions, so that such a use is preferable. For this reason, the ionic solid of the present invention can also be molded into pellets. Even when pellets are formed, a decrease in the ionic conductivity is presumed difficult to occur because cations flow through the "pathway" formed by anionic heterometallic complexes.

The size of the "pathway" is determined by the diameter of the anionic heterometallic complex used in the present invention. The size of flowing cationic ions needs to be considered, and it is preferable to use an anionic heterometallic complex having a diameter of at least 1.5 nm or more and preferably 2 nm or more, for forming the "pathway" having the nature of the present invention.

An ionic solid of the present invention is represented by Formula (1) below:

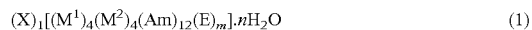

$$(X)_l[(M^1)_4(M^2)_4(Am)_{12}(E)_m] \cdot nH_2O \quad (1)$$

wherein $M^1$ is Ir, Rh, Co, Os, Ru, Fe, Ni, Cr, or Mn;

$M^2$ is Zn, Cd, Hg, Au, or Cu (provided that when is Rh, $M^2$ is not Zn);

X is a cation;

Am is an amino acid;

E is $O^{2-}$, $S^{2-}$, $Se^{2-}$, $Te^{2-}$, $F^-$, $Cl^-$, $Br^-$, or $I^-$;

l is a number ranging from 4 to 14 when multiplied by an ionic valence of X;

m is a number of 0 or 1; and n is a number ranging from 1 to 100.

Further, the anionic heterometallic complex in the ionic solid of the present invention is represented by Formula (2):

$$[(M^1)_4(M^2)_4(Am)_{12}(E)_m]^{1-} \quad (2)$$

wherein $M^1$, $M^2$, X, Am, F, l and m are the same as defined above.

$M^1$ is preferably Co and Rh, and is more preferably Rh, from the viewpoint of cation adsorption capacity and ionic conduction properties. Further, $M^2$ is, from the viewpoint of cation adsorption capacity and ionic conduction properties, preferably Ag, Cu and Zn, more preferably Ag and Zn, and further preferably Ag.

The above metals affect the stability of the anionic heterometallic complex. Particularly, the combination of metals $M^1$ and $M^2$ is preferable from the viewpoint of increasing the number of nuclei, i.e., increasing the size, of the anionic heterometallic complex. Consequently, this affects the cation adsorption capacity and ionic conduction properties.

X is a cation. X is typically a metal cation and may be a typical metal or a transition metal including a lanthanoid. Of these, a cation of a metal belonging to Group 1 or Group 2 is preferable. Specific examples of X in the case of the typical metal include $Li^+$, $Na^+$, $K^+$, $Rb^+$, $Cs^+$, $Be^+$, $Mg^{2+}$, $Ca^{2+}$, $Sr^{2+}$, $Ba^{2+}$ and $Ra^{2+}$, and $Na^+$, $K^+$, $Rb^+$, $Cs^+$, $Mg^+$, $Ca^+$, $Sr^{2+}$ and $Ba^{2+}$ are more preferable. These cationic species are advantageous because, in the aspect of ionic fluidity, electrostatic interaction against the anionic heterometallic complex is small. Additionally, an optimal cationic species, as an ion exchanger, can be selected depending on an ion species to be exchanged. Further, there is also a case where those having higher valences such as $Al^{3+}$ and $Ti^{4+}$ are preferable according to uses of the ionic solid.

The present inventors consider that, in the ionic solid of the present invention, the reaction in which a cation forms a coordinate bond with water or a carboxyl group coordinated around a complex anion and leads to the cleavage of these coordinate bonds and the ion migration is a rate-determining step of the mechanism demonstrating the ionic fluidity. A sufficiently fast exchange rate of the coordinate bonds between cations and water or carboxyl groups refers to a fast migration speed, and the viewpoint therefrom, alkali metal monovalent cations such as potassium and sodium are further preferable. On the other hand, ions having large ionic valence and transition metal ions having ligand field stabilization energy are slow in exchange reaction thereby exhibiting a tendency of reducing the performance as an ionic conductor and an ion exchanger.

1 is a number ranging from 4 to 14 when multiplied by an ionic valence of X. For example, when X is a metal ion belonging to Group 1, l is a number ranging from 4 to 14. When X is a metal ion belonging to GROUP 2, l is a number ranging from 2 to 7. An ion product ranging from 4 to 14 is advantageous in the aspect of a large mobile electric charge.

Am represents a ligand coordinated to $M^1$ and $M^2$ to form a stable anionic heterometallic complex. For the ligand, a known ligand can also be used. Cross-linked functional groups such as a hydroxy group, an imidazole group and a carboxyl group do not always have a strong metal-ligand bond in water, due to which it should be cautious not to affect the purpose of the present invention when used. A multidentate ligand having a plurality of coordination sites to metal ions can form coordinate bonds to metal ions in the form of a stable chelate structure. Particularly, it is preferable that a thiol group capable of stably forming a metal-ligand bond in water is present, and an amino acid having a thiol group is more preferable. The relative position between an amino group and a carboxyl group is not limited, and a carboxyl group may be at the ω-position, in addition to the α-amino acid. Additionally, an amino group and a thiol group are preferably positioned to form a chelate structure to a metal, and more preferably positioned at the β-position or the γ-position of a carboxyl group. For such an amino acid, cysteine, penicillamine and homocysteine are specifically preferable, with cysteine and penicillamine being preferable.

E is an anion and represents $O^{2-}$, $S^{2-}$, $Se^{2-}$, $Te^{2-}$, $F^-$, $Cl^-$, $Br^-$ or $I^-$. For E, $O^{2-}$, $S^{2-}$, $Cl^-$ and $Br^-$ are more preferable, and $O^{2-}$ and $S^{2-}$ are further preferable. m is a number of 0 or 1, and when m is 0, E is absent. E is present for filling and stabilizing the coordination sphere of a metal ion forming the anionic heterometallic complex.

n is a number ranging from 1 to 100. n preferably ranges from 1 to 80, more preferably from 20 to 80, and further preferably from 30 to 60. n, as an amount of a medium for allowing X (cationic species) to pass through, is adjusted such that the fluidity is increased depending on the kind of the anionic ligand and the kind of the cationic species. n can be adjusted by the temperature, time and the like of isolation operation after complex formation.

Examples of the preferable combination of $M^1$ and $M^2$ include Rh and Ag, Co and Zn, Co and Ag, and Rh and Cu, and further preferably Rh and Ag, Co and Zn, and Co and Ag. When in these combinations, the contamination of $M^1$ and $M^2$ does not occur, so that a stable anionic heterometallic complex can be formed.

Specific examples of the ionic solid of the present invention include the following:

$(X)_1[(Rh)_4(Ag)_4(cys)_{12}] \cdot nH_2O$;

$(X)_1[(Co)_4(Zn)_4(cys)_{12}] \cdot nH_2O$; and $(X)_1[(Co)_4(Ag)_4(cys)_{12}] nH_2O$ (x, l and n are as defined above).

In the ionic solid of the present invention, 3 components, $M^1$, $M^2$ and Am are coordinated in a ratio of 4:4:12. More specifically, as shown in FIG. 1, 3 molecules of Am are coordinated to 1 molecule of $M^1$, to which $M^2$ is reacted, thereby to form a structure of $M^1:M^2:Am=4:4:12$. Optionally, 1 anion of E is present in the center of 4 metals of $M^2$. Furthermore, the ionic solid (1) is an ionic solid having a crystal structure as shown in FIG. 2.

More specifically, the ionic solid of the present invention is different from naturally occurring ionic solids but an ion-fluid type ionic solid wherein a cationic species $((X)_1)$ flows through an interstice in the crystal lattice formed by an anionic heterometallic complex $[(M^1)_4(M^2)_4(Am)_{12}(E)_m]$ by a non-Coulomb force.

The size of the crystal lattice formed by anionic heterometallic complexes is typically from 1 to 10 nm, preferably from 2 to 6 nm, and further preferably from 2 to 3 nm.

The ionic solid (1) can be produced by, for example, reacting an amino acid (Am) with a metal $M^1$, subsequently reacting a metal $M^2$ therewith, and further reacting a cation (X) therewith.

The reaction of $M^1$ and an amino acid can be carried out by, for example, stirring $M^1$ and the amino acid in a solvent such as a basic aqueous solution. $M^1(Am)_3$ can be obtained by this reaction. The reaction of $M^1(Am)_3$ and $M^2$ can be carried out by, for example, stirring in a solvent such as water or an acetic acid/potassium acetate buffer solution. Next, the reaction of the obtained compound and a cation is carried out by adding an inorganic salt of the cation or the like in water.

The isolation operation of the obtained ionic solid (1) is carried out by, for example, adding ethanol/methanol or adding an excessive amount of cation salt and allowing the resulting mixture to stand in a cool, dark place.

The ionic solid (1) of the present invention demonstrates a good ionic conductivity even in the presence of water and air. Further, the ionic solid of the present invention can be molded into a molded product such as a pellet without heating at all and has an extremely high ionic conductivity in the state of a molded product, thus being useful particularly as a solid ionic conductor such as a solid electrolyte. On the other hand, the ionic conductivity of the metal complexes described in Non Patent Literatures 1 to 3, when molded into a pellet, is lower than that of the ionic solid of the present invention.

Thus, the ionic solid (1) of the present invention is applicable to various electrochemical devices. Examples of such an electrochemical device include an ion secondary battery, an electrochromic element, and a thermoelectric element.

Examples of the ion secondary battery herein include, lithium-ion secondary batteries and sodium ion secondary batteries. For obtaining an ion secondary battery, a layer containing a positive-electrode active substance at a positive electrode, a layer containing a carbon material and the like at a negative electrode, and a layer containing an ionic solid (solid electrolyte) of the present invention therebetween may be provided. The ionic solid of the present invention is a stable solid electrolyte even in the presence of water and vapor, and thus this ion secondary battery is useful as an all-solid ion secondary battery. Additionally, the ionic solid of the present invention has a high conductivity not only to lithium ion but also to sodium ion and potassium ion thereby to be produced as an all-solid lithium-ion secondary battery and an all-solid sodium ion secondary battery.

For obtaining an electrochromic element, an ionic solid of the present invention as a solid electrolyte and a composition containing an electrochromic compound may be positioned between a pair of electrodes. The electrochromic compound herein is a substance wherein optical absorption properties such as a colored state and light transmittance of the substance are changed by electrochemical redox reaction and examples include compounds described in International Publication No. WO2012/169093.

The present inventors found that the ionic solid (1) of the present invention has a fast cation exchange capacity (cation separation capacity). More specifically, the ionic solid (1) has cations (X), and such a cation has the property of being easily and rapidly exchanged with other cations. Accordingly, the ionic solid (1), when used, can be used as a separating agent of cations such as radioactive cesium ions present in the environment. Examples of the ion exchangeable cation include metal cations belonging to Group 1 or Group 2, such as $Li^+$, $Na^+$, $K^+$, $Rb^+$, $Cs^+$, $Be^{2+}$, $Mg^{2+}$, $Ca^{2+}$, $Sr^{2+}$, $Ba^{2+}$ and $Ra^{2+}$.

When the ionic solid (1) of the present invention is used as a cation exchange agent or a cation separating agent, the ionic solid (1) of the present invention may be used in the form of crystal or may be used in the form of pellet. The ionic solid (1) of the present invention fast exchanges, when cations are present therearound, those cations therearound with the cations (X) in the ionic solid structure. Thus, when a solution in which cations to be separated are present is in contact with the ionic solid (1) of the present invention, cations therearound can be separated.

EXAMPLES

The present invention is further described in detail in reference to examples.

Example 1 (Production of an Ionic Solid)

(1) Production of $Li_8[(Rh)_4(Ag)_4 (L-cys)_{12}]$ $Li_8[(Rh)_4(Ag)_4(L-cys)_{12}]$ was produced by the reaction as shown in FIG. 1.

50 mg of $\Delta_{LLL}$-$H_3[Rh(L-cys)_3]$ was suspended in 5 mL of water, and 0.62 mL of 0.5M LiOH was added thereto to obtain a yellow solution. To this solution, a colorless solution in which 19 mg of silver nitrate was dissolved in 2.5 mL of water was added and stirred, thereby instantly turning into a dark red solution. This solution was stirred for about 10 minutes and subsequently ethanol was vapor-diffused for several days to obtain the substance of interest in the form of dark red crystals. The isolation yield was 48%.

$\Delta_{LLL}$-$H_3[Rh(L-cys)_3]$ is synthesized by the method described in Bull. Chem. Soc. Jpn. 1990, 63, 792 or Inorg. Chem. 1994, 33, 538-544.

The crystal structure of the obtained ionic solid was shown in FIG. 2.

(2) The following ionic solids were produced in the same manner.

$Na_8[(Rh)_4(Ag)_4(L-cys)_{12}]$ $K_8[(Rh)_4(Ag)_4(L-cys)_{12}]$ $Rb_8[(Rh)_4(Ag)_4(L-cys)_{12}]$ $Cs_8[(Rh)_4(Ag)_4(L-cys)_{12}]$ $Mg_8[(Rh)_4(Ag)_4(L-cys)_{12}]$ $Ca_4[(Rh)_4(Ag)_4(L-cys)_{12}]$ $Ba_4[(Rh)_4(Ag)_4(L-cys)_{12}]$ $Mn_4[(Rh)_4(Ag)_4(L-cys)_{12}]$ Example 2

(1) Production of $K_6[(Co)_4(Zn)_4(L-cys)_{12}O]$ 5 g of $\Delta_{LLL}$-$K_3[Co(L-cys)_3]$ was dissolved in 100 mL of an aqueous solution of 0.5M potassium acetate, which was then cooled to a freezing temperature, and subsequently 0.7 g of zinc chloride was added to instantly obtain a dark purple solution. At this time, suspension may occur, and in such an occasion, the precipitate is filtered out. This solution was stirred for 20 minutes under ice cooling and subsequently 50 mL of ethanol was added thereto to produce a purple powder as a coarse powder of the substance of interest. This coarse powder was dissolved in 20 mL of water and the insolubles were removed, subsequently 20 mL of an aqueous solution of saturated potassium chloride was added and the resulting mixture was allowed to stand in a refrigerator, to obtain the substance of interest in the form of dark purple crystals. The isolation yield was 14%.

$\Delta_{LLL}$-$K_3[Co(L-cys)_3]$ is synthesized by the method described in J. Chem. Soc., Dalton Trans. 1999, 1221.

Example 3

(1) Production of $K_8[(Co)_4(Ag)_4 (L-cys)_{12}]$ 0.3 g of $\Delta_{LLL}$-$K_3[Co(L-cys)_3]$ was dissolved in water (30 mL) and an aqueous solution of 0.1 M silver nitrate (3.1 mL) was added thereto to obtain a dark reddish brown solution. This solution was stirred for 15 minutes at room temperature and subsequently 90 mL of ethanol was added thereto to obtain a red powder as a coarse powder of the substance of interest. The isolation yield was 36%.

As in the above section, $\Delta_{LLL}$-$K_3[Co(L-cys)_3]$ is synthesized by the method described in J. Chem. Soc., Dalton Trans. 1999, 1221.

Example 4 (Measurement of Ion Exchange Capacity)

A solution of 0.1 M cesium acetate (Solution A) was prepared using a mixed solution of water/ethanol (1/3) as a solvent. 0.1 g of $K_6[Zn_4Co_4(L-cys)_{12}O]$ powder was added to 50 mL of Solution A and the resulting mixture was allowed to stand. At this time, the powder was not dissolved. A part thereof was filtered off at each time elapsed and washed respectively with the mixed solution of water/ethanol (1/3). The obtained samples were weighed, dissolved in 0.6 mL of heavy water, and measured for $^{133}Cs$ NMR spectrum. An intensity of $^{133}$Cs signal was converted into a concentration using an external standard sample to determine the number of moles of cesium ions contained in the powder.

The obtained results are shown in FIG. 3. It was revealed that all K$^+$ ions were exchanged with Cs$^+$ ions in 60 minutes from the powder was added.

Further, it was proved that the ionic solid of the present invention has not only the K$^+$/Cs$^+$ exchange capacity but also the ion exchange capacities among Na$^+$, Li$^+$, Mg$^{2+}$, Mn$^{2+}$, and Sr$^{2+}$. Particularly, the ion exchange capacities among K$^+$, Na$^+$, Li$^+$, and Cs$^+$ were intense.

Example 5 (Measurement of Ionic Conductivity)

(1) Making Pellets

About 10 to 20 mg of a powder or crystalline sample was packed in a 3 mmφ cylindrical cell and held for 20 minutes or more under a pressure of 5 GPa to make pellets.

(2) Measurement of Ionic Conduction Properties

The pellets obtained by the method of the previous section were pressure-bonded to a SH-Z cell holder, produced by TOYO Corporation. The entire cell holder connected to cables was allowed to stand in a thermostat in which humidity and temperature were adjusted. In this condition, using Wayne Kerr 6430B Component Analyzer, alternating current impedance was measured by a pseudo four-terminal method within the frequency range of from 500 kHz to 20 Hz.

When a Nyquist plot was made for the obtained alternating current impedance with the real part (Z') being a horizontal axis and the imaginary part (Z'') being a vertical axis, a semicircular shape derived from bulk ionic conduction was drawn. This diameter was defined as a bulk resistance (R) derived from the ionic conduction thereby to calculate a resistivity of all the samples.

FIG. 4 shows measurement results of ionic conductivities (σ/Scm$^{-1}$) of 3 kinds of pellet samples made of the ionic solid of the present invention.

On the other hand, ionic conductivities (σ/Scm$^{-1}$) at 25° C. of the pellets which used Li$_6$[Zn$_4$Rh$_4$(L-cys)$_{12}$O] described in Non Patent Literatures 1 to 3 were measured and found to be 2×10$^{-8}$ Scm$^{-1}$ (Li$^+$), which were lower than the ionic solid (1) of the present invention.

Example 6 (Humidity Dependency of Ionic Conductivity)

Ionic conductivities were measured using K$_8$[Rh$_4$Ag$_4$(L-cys)$_{12}$] and Li$_8$[Rh$_4$Ag$_4$(L-cys)$_{12}$] in the same manner as in Example 5 under different humidity conditions. The results are shown in FIG. 5.

As a result, it was proved that the ionic conductivity of the ionic solid (1) of the present invention did not decrease even under high humidity conditions.

The invention claimed is:

1. An ionic solid, wherein an anionic heterometallic complex aggregates to form a crystal lattice in which a cationic species is present in an interstice in the crystal lattice,
wherein the anionic heterometallic complex is a complex represented by Formula (2):

$$[(M^1)_4(M^2)_4(Am)_{12}(E)_m]^{1-} \quad (2)$$

wherein
M$^1$ is Ir, Rh, Co, Os, Ru, Fe, Ni, Cr or Mn;
M$^2$ is Zn, Cd, Hg, Au, Ag or Cu provided that when M$^1$ is Rh, M$^2$ is not Zn;
Am is an amino acid;
E is O$^{2-}$, S$^{2-}$, Se$^{2-}$, Te$^{2-}$, F$^-$, Cl$^-$, Br$^-$ or I$^-$;
l is a number ranging from 4 to 14 when multiplied by an ionic valence of cation; and
m is a number of 0 or 1.

2. An ionic conductor comprising the ionic solid according to claim 1.

3. A solid electrolyte comprising the ionic solid according to claim 1.

4. An electrochemical device comprising the ionic conductor according to claim 2.

5. The electrochemical device according to claim 4, which is an electrochemical device selected from the group consisting of an ion secondary battery, an electrochromic element and a thermoelectric element.

6. A cation separating agent comprising the ionic solid according to claim 1.

7. The cation separating agent according to claim 6, which is a radioactive cesium ion separating agent.

8. An ionic solid represented by Formula (1):

$$(X)_1[(M^1)_4(M^2)_4(Am)_{12}(E)_m] \cdot nH_2O \quad (1)$$

wherein M$^1$ is Ir, Rh, Co, Os, Ru, Fe, Ni, Cr or Mn;
M$^2$ is Zn, Cd, Hg, Au, Ag or Cu provided that when M$^1$ is Rh, M$^2$ is not Zn;
X is a cation;
Am is an amino acid;
E is O$^{2-}$, S$^{2-}$, Se$^{2-}$, Te$^{2-}$, F$^-$, Cl$^-$, Br$^-$ or I$-$;
l is a number ranging from 4 to 14 when multiplied by an ionic valence of X;
m is a number of 0 or 1; and
n is a number of from 1 to 100.

9. The ionic solid according to claim 8, wherein Am is an amino acid having a thiol group.

10. The ionic solid according to claim 8, wherein X is a cation of a metal belonging to Group 1 or Group 2.

11. The ionic solid according to claim 8, wherein M$^1$ is Rh and M$^2$ is Ag, M$^1$ is Co and M$^2$ is Ag, or M$^1$ is Co and M$^2$ is Zn.

12. The ionic solid according to claim 8, wherein Am is an amino acid selected from the group consisting of cysteine, penicillamine and homocysteine.

* * * * *